(12) United States Patent
Terwee et al.

(10) Patent No.: US 8,388,601 B2
(45) Date of Patent: Mar. 5, 2013

(54) VISCOELASTIC SOLUTION OR GEL FORMULATION, AND METHODS OF TREATING A BODY SITE WITH THE SAME

(75) Inventors: Thom Terwee, Roden (NL); Sverker Norrby, Leek (NL); Robert Shimizu, Laguna Niguel, CA (US); Rolf Bergman, Uppsala (SE)

(73) Assignee: AMO Groningen B.V., Groningen (NL)

( * ) Notice: Subject to any disclaimer, the term of this patent is extended or adjusted under 35 U.S.C. 154(b) by 1477 days.

(21) Appl. No.: 11/233,295

(22) Filed: Sep. 21, 2005

(65) Prior Publication Data

US 2006/0064163 A1 Mar. 23, 2006

Related U.S. Application Data

(60) Provisional application No. 60/613,088, filed on Sep. 23, 2004.

(30) Foreign Application Priority Data

Sep. 21, 2004 (SE) ..................................... 04022729

(51) Int. Cl.
*A61M 31/00* (2006.01)
*A61M 35/00* (2006.01)
*A61F 2/16* (2006.01)
(52) U.S. Cl. ......................... 604/521; 604/294; 623/6.13
(58) Field of Classification Search .................. 128/898; 623/6.37, 6.56, 905; 424/427; 427/2.21
See application file for complete search history.

(56) References Cited

U.S. PATENT DOCUMENTS

| 4,965,253 A | * | 10/1990 | Goldberg et al. ........... 424/78.36 |
| 5,627,162 A | | 5/1997 | Gwon et al. |
| 5,681,825 A | * | 10/1997 | Lindqvist et al. ............... 514/54 |
| 6,063,116 A | | 5/2000 | Kelleher |
| 6,228,807 B1 | * | 5/2001 | Kuchikata et al. ............ 504/206 |
| 6,558,688 B2 | | 5/2003 | Saishin et al. |
| 2003/0014021 A1 | * | 1/2003 | Holmen ........................ 604/294 |
| 2004/0086479 A1 | | 5/2004 | Grinstaff et al. |
| 2004/0258729 A1 | | 12/2004 | Czernuszka et al. |

FOREIGN PATENT DOCUMENTS

| EP | 0 244 178 A2 | 11/1987 |
| EP | 0 555 898 A2 | 8/1993 |
| WO | WO 96/34629 | 7/1996 |
| WO | WO 02/15828 A2 | 2/2002 |
| WO | WO 2005/054440 A2 | 6/2005 |

* cited by examiner

*Primary Examiner* — Thomas J Sweet
*Assistant Examiner* — Joshua Levine
(74) *Attorney, Agent, or Firm* — AMO Groningen B.V.

(57) ABSTRACT

The invention relates to method of preparing a viscoelastic therapeutic liquid comprising a viscoelastic agent and a homogenously distributed therapeutically active agent, wherein the therapeutically active agent is distributed throughout the viscoelastic compound when the viscoelastic compound is in dry form. In one embodiment of the invention, the viscoelastic compound in dry form is mixed with an aqueous solution of the therapeutically active agent. The invention further relates to utilities of homogenous viscoelastic compositions in therapeutic applications including ophthalmic surgery.

5 Claims, 1 Drawing Sheet

VISCOELASTIC SOLUTION OR GEL FORMULATION, AND METHODS OF TREATING A BODY SITE WITH THE SAME

RELATED APPLICATIONS

This application is the utility application which claims priority to Swedish Application No. 0402272-9, filed on Sep. 21, 2004, and to U.S. Provisional Application No. 60/613,088, filed on Sep. 23, 2004, and which are incorporated herein.

FIELD OF THE INVENTION

The present invention relates to a method of preparing a gel or a viscoelastic therapeutic liquid agent and the utility of such agent in ophthalmic surgical processes and other therapeutic fields requiring highly homogenous formulations of polymers and therapeutic components in viscoelastic solution or gel state including therapeutic agents.

BACKGROUND OF THE INVENTION

Cataract extraction is among the most commonly performed operations in the world. The natural lens is located within a capsular bag, also called lens capsule or capsular sac, which is located in the posterior chamber of the anterior segments of the eye. In order to gain access to the natural lens, an incision is made either in either the clear cornea, at the limbus, or in the sclera of the eye whereby it becomes possible to introduce surgical instruments into the anterior segments of the eye. In the case of cataract extraction, an opening is made in the capsular bag, currently mostly by a capsular a capsulorhexis technique, whereby a portion of the anterior membrane of the capsular bag is torn out to allow insertion of surgical instruments into the capsular bag for the purpose of extraction of the natural lens. The natural lens can be removed through by application of many known techniques, including what is known as phacoemulsification.

Phacoemulsification is a method that entails the application of ultrasonic energy or other forms of energy to the natural lens thus breaking said lens into fragments, which can then be aspirated from the capsular bag. The capsular bag remains substantially intact throughout the process of cataract extraction, with the exception of the portion removed to prepare access for the surgical instruments used in the extraction of the natural lens. After the removal of the natural lens (aphakia), an artificial intraocular lens (IOL) implant is implanted within the capsular bag in order to mimic the transparency and the refractive function of a natural lens. Alternatively a lens material is injected to fill the capsular bag and thus an artificial lens is created in situ. Such lenses (ACL) can in addition restore the accommodative function of the natural lens before the onset of presbyopia (loss of ability to accommodate).

In modern cataract extraction surgery, especially with phacoemulsification, one feature of the surgical technique is to separate the natural lens from the capsular bag, one such a technique is hydrodissection. In this technique a fluid wave is injected under the anterior capsule in such a way that it separates the lens from the capsular bag. One of the most common used fluids for the purpose of hydrodissection is a balanced salt solution, which is both ionically and osmotically balanced with regard to the aqueous humor and internal tissue of the eye. In addition to sodium chloride, said solution contains also potassium chloride, calcium chloride, magnesium chloride, sodium acetate and sodium citrate. The balanced salt solutions are considered to be physiologically compatible with the ocular tissue since they contain the essential ions for normal cell metabolism.

Lens removal with IOL or ACL implantation replacement provides significant benefits to most cataract patients. Currently lens removal with artificial lens implantation is increasingly carried out in a non-catarcatous eye, so-called refractive lens exchange, often with the purpose to relieve presbyopia. However, it is estimated that up to fifty percent of all patients, who have implants placed within the capsular bag, will develop capsular opacification (CO), also known as secondary cataract or aftercataract, within five years after surgery. CO is an opacification located on the inner surface of capsular bag, whether located posteriorly (PCO) or anteriorly (ACO). CO is caused by deposition or ingrowth of cells, cell derivatives and/or fibers into the visual axis and might also be caused by extracellular matrix produced by the lens epithelial cells, thereby impairing the optical axis of the eye and thus clouding of the vision. Thus, the cell deposits on the capsule and/or on the implant originate from the proliferation and migration of residual lens epithelial cells on the interior surface of the capsular bag and the production of extracellular matrix by these cells. During cataract surgery, the surgeon removes the lens and replaces it with a new artificial lens.

Ophthalmic surgeons, aware of the problems associated with residual lens epithelial cells, typically take considerable care in trying to remove as many as possible of the lens epithelial cells prior to implantation of an artificial lens (IOL or ACL). However, despite these efforts, a significant number of lens epithelial cells are usually left on the interior surface of the capsular bag since these cells are difficult to view and often difficult to reach and virtually impossible to completely remove.

The most common treatment for postoperative PCO uses laser energy, which is applied to the posterior membrane of the capsular bag for the purpose of creating an opening in the posterior capsule (known as Nd-YAG capsulotomy). However, the laser energy applied to the posterior membrane of the capsular bag is ordinarily directed through the implant and might damage the optic of said implant. Accordingly, it is preferred to prevent the occurrence of CO rather than treating CO at a later date through the application of laser energy. This is especially desirable when the implant is accommodating response to ciliary muscle contraction, in which case a capsulotomy may compromise the accommodative ability of the lens Various procedures for the prevention of CO have been suggested in recent years. These include administration of antimetabolites (such as 5-flurouracil, adunomycin and doxorubicin), irrigation with hypotonic solutions, irrigation with chelating agents, administration of cytotoxic agents (such as saporin) conjugated to target seeking molecules like polylysine, antibodies and fibroblast growth factors. However, few if any of these procedures have proven to be particularly successful in the prevention of CO due to the fact that it is extremely difficult to destroy residual lens epithelial cells without simultaneously destroying other cells within the eye, e.g. there exists a number of chemical agents that could kill the lens epithelial cells, however, said agents may also adversely affect other cells within the eye, in particular corneal endothelial cells. Thus, selective destruction of residual lens epithelial cells by exploitation of the cells increased proliferate activity has thus been the primary approach for the prevention of CO. Many of these suggested therapies would also be costly and difficult to reliably apply on consistent basis.

Antimetabolites such as 5-fluorouracil (5FU) and daunomycin have been injected into the capsular bags of eyes in attempts to prevent CO. However, for antimetabolite therapy to be effective, the agents must be present when the residual lens epithelial cell proliferation resumes at an indeterminate time following surgery. Sustained drug delivery systems have also been investigated as means for preventing CO. However, the effective time frame within when to apply these agents may likewise be difficult to determine. Thus, timing is difficult in the prevention of CO since it, as mentioned above, is believed to result primarily from the propagation of residual lens epithelial cells of the germinal layer and it is difficult to accurately predict when said cells might start to proliferate and migrate across the capsular bag into the optical zone.

In order to reduce risks of contacting other eye tissues with hazardous agents WO 02/15828 (Bausch and Lomb) suggests to seal the capsular bag with the lens removing instrument by means of which PCO treating agents can be introduced methods for removing epithelial cells by injecting a composition comprising an agent after the natural lens has been removed from the capsular bag.

Another approach to obtain control of the PCO treatment step would be to use a viscoelastic solution or a gel which can be introduced and removed with adequate control compared to plain solutions. The viscoelastic solutions or gels can also serve to maintain the concentration of the agent as disclosed in U.S. Pat. No. 5,110,090 (Krumeich) or to protect the tissues of the anterior chamber from agents injected into the capsular bag as disclosed in U.S. Pat. No. 4,909,784 (Dubroff). U.S. Pat. No. 5,061,696 (York) suggests to fill the lens free capsular bag with air and then inject a hypotonic viscoelastic that is capable to rupture unwanted epithelial cells with osmotic swelling. WO 96/34629 suggests a sustained release preparation of cytotoxic agent complexed to hyaluronic acid that is implanted in a suitable position following the surgical process. None of these techniques provide a satisfying solution to completely inhibit postsurgical growth of epithelial cells. For capsular opacification treatment with viscoelastic, the present inventors have experienced uneven results such that certain parts of the inner capsular bag appear inadequately treated resulting in epithelial cell growth in strains. Apparently, there is still a need of a reliable and safe way of preventing capsular opacification in conjunction with a surgical process for lens replacement.

DETAILED DESCRIPTION

Figure 1:
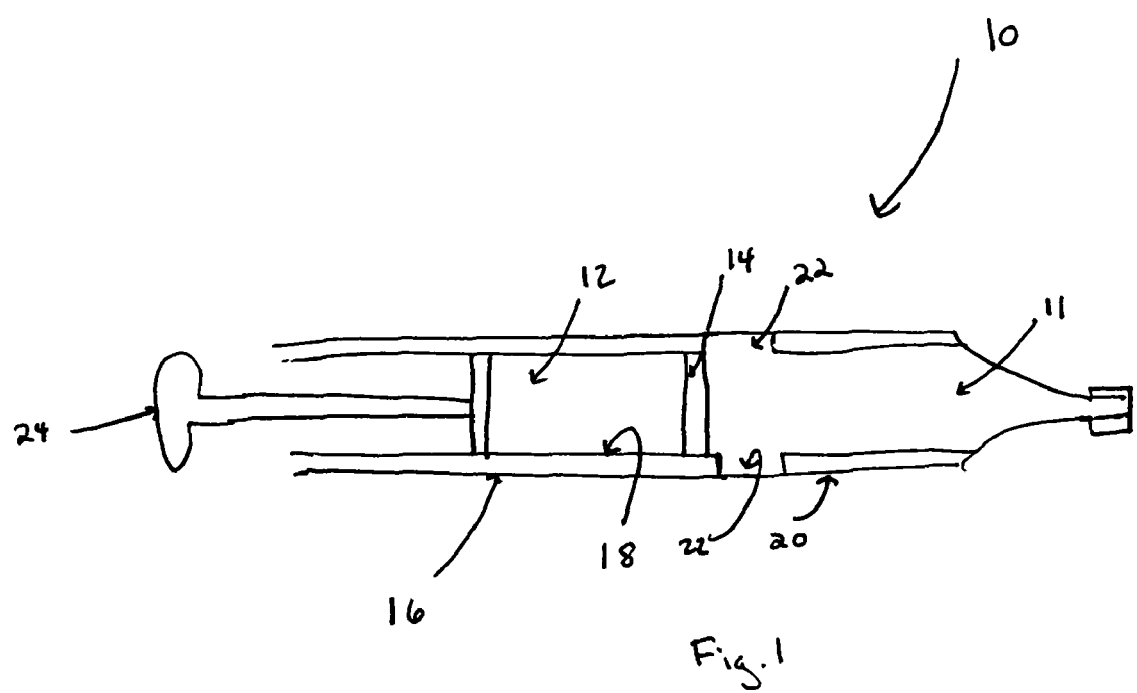
FIG. 1 is a view of a syringe which may be used to deliver a solution according to the present invention.

In its most general terms the objects of the present invention is to provide for a method and composition that enables correct administration of a therapeutically active agent to a body surface when applied locally in an aqueous environment.

More specifically, the object of the present invention to provide for a therapy for preventing capsular opacification which ensures that the active agent that affects the epithelial cells has a correct concentration over the entire inner surface of the capsular bag.

These objectives are met with a viscoelastic therapeutic composition or a gel, wherein the therapeutically active agent is homogenously distributed. To obtain adequate homogeneity, it has been found necessary to mix a solution of the active agent with the dry polymer substances used for formulating the gels or the viscoelastic solutions.

According to a first general embodiment, the present invention refers to a viscoelastic preparation or gel including an active agent homogeneously distributed therein. The preparation may be formed by drying the viscoelastic agent, and then homogeneously distributing the active agent therein. Such homogeneous distribution may be accomplished by a number of means including, but not limited to, (a) mixing a viscoelastic compound in dry form with a solution of the active agent, (b) using particle aggregation techniques, (c) spray coating the viscoelastic compound in dry form with the active agent, (d) fluidized bed pelletizing, (e) Fluid bed pelletizing, (f) container blending, (g) fluid bed granulation, (h) fluid bed coating, (i) spheronizing, (j) drum coating, (k) sieve technologies, (l) wet granulation, (m) semi-continuous granulation, and/or (n) fluid bed drying.

One of ordinary skill in the art will realize that the term 'mixture' as utilized herein encompasses traditional mixtures as well as aggregated and/or coated particles.

According to a second general embodiment, the present invention refers to a method of locally treating a body site with a viscoelastic preparation or gel including a therapeutically active agent wherein said composition has the active agent homogeneously distributed in said viscoelastic preparation or gel. The method comprises the steps of forming a homogeneous preparation comprising a viscoelastic compound or gel and an active agent, applying the homogenous preparation to the body site for a time sufficient for the active agent to exert its activity and removing the preparation from the body site.

In a more specific embodiment, the present invention refers to a method of preventing posterior chamber opacification following cataract surgery. At first the anterior chamber of the eye is injected with a first viscoelastic solution with suitable properties to protect the eye tissues during the following surgical steps, whereupon the defective lens or cataract lens is removed. So far conventional techniques can be applied. After optionally conducting conventional rinsing measures of interior capsular bag a second viscoelastic composition or gel comprising active agents that is prepared in accordance with the present invention is introduced. The second solution may have the same viscoelastic properties as the first solution, or may be designed to have different viscoelastic properties. The inner wall of the capsular bag is contacted with the second viscoelastic composition or gel for a time sufficient to effective kill remaining epithelial cells. Generally, this time is a few minutes. Assuming appropriate concentration of the active agent, this time is preferably less than five minutes. Subsequently, the second viscoelastic agent can be removed from the eye. Preferably by a standard syringe equipment inserted through the first viscoelastic preparation which acts as a shield for inadvertent exposure of active agents to the surrounding eye tissues. From that point the surgical process can be finalized according to standard procedures well know in ophthalmic surgery.

As used herein, the term viscoelastic compound is intended to encompass any compound having viscoelastic properties including, but not limited to, cellulose polymers and their derivatives (for example, hydroxypropyl methyl cellulose) and polysaccharides including, but not limited to, glycosamino glycans such as hyaluronic acid and synthetic linear polymers. By way of example, the viscoelastic compound may be chondroitin sulphate, polyacrylamide, collagen, pectin, synthetic polymer-modified carbohydrate, hyaluronic acid or salts or esters thereof in essentially pure form and dry form, or mixtures of two or more of these compounds. One of ordinary skill in the art will be able to select the appropriate viscoelastic agent based on the use for which the solution is made. For example, if a solution is intended to be used in an area of the body where control of sodium concentration is a concern, then the user may prefer to use a viscoelastic compound that is not a sodium salt. For example, the user may prefer to use hydroxypropyl methyl cellulose as opposed to sodium hyaluronate.

When the present invention is intended to be used on or in a body site where infection is a concern, the solution may be sterilized. One of ordinary skill in the art will recognize that sterilization frequently results in the reduction in average molecular weight of the viscoelastic solution, and will be able to accommodate this in the selected formulation to achieve the intended viscoelastic properties.

Suitable sodium hylauronates may in one aspect have a molecular mass of at least 5-6 million before sterilization which when dissolved to a 1% (w/w) solution will obtain similar characteristics as Healon® ophthalmic viscoelastic solution (OVD)(available from Advanced Medical Optics, Inc., Santa Ana, Calif.), or when dissolved to 2.3% (w/w) will resemble Healon® 5 OVD (available from Advanced Medical Optics, Inc., Santa Ana, Calif.)). The preparation and purification of this type of sodium hyaluronate and to generate viscoelastic solutions are described in more detail in U.S. Pat. Nos. 4,141,973 and 6,086,697. Also high viscosity, high molecular mass sodium hyaluronates such as those described in U.S. Pat. No. 5,681,825 (marketed as viscoelastic under the trade name Healon® GV) can be used with the present invention. One of ordinary skill in the art will realize that, in other aspects of the invention, suitable sodium hylauronates may have a lower molecular mass, as low as 100,000 Da. Clearly, the desired molecular weight is dependent on the class of polymer that is desired to be used in association with the present invention. By way of example, and not of limitation, suitable viscoelastic solutions may be formed using HPMC in the weight range of from about 30,000 to about several hundred thousand daltons. Similarly, suitable viscoelastic solutions may be formed using chondroitin sulphate in the weight range starting from about 20,000 to about 30,000. In general, the molecular weight of the chosen viscoelastic compound (whether it is sodium hyaluronate, HPMC or another viscoelastic) will be selected based on the desired viscoelastic properties of the final solution.

Preferably, the polymer for formulating the viscoelastic solutions or gels is in dry form. By 'dry', it is meant that the viscoelastic compound is not in solution, and has been dried to a stringy, granular, flaky or powdered appearance.

It is understood that dry viscoelastic compounds will contain water in an amount related to the environment in which it is located. For example, when sodium hyaluronate is used, the dry sodium hyaluronate will typically comprise from about 10 to about 15% (w/w) water. Sodium hyaluronate is extremely hygroscopic and will if dried to lower moisture content rapidly absorb ambient water to a flaky, fibrous appearance.

A number of exemplars of methods which may be used to prepare solutions according to the present invention are discussed in brief detail below. These are provided by way of example only, and are not intended to be limiting.

Mixing

A solution according to the present invention may be prepared by mixing. In such an instance, the dry viscoelastic compound is mixed using a low shear method with a solution of the active agent (or agents) for a time sufficient to obtain a suitable homogeneity and a product free from air bubbles or air pockets. The active agent solvent may be water. Alternatively, the active agent may be dissolved in a different solvent. If this is the case, preferably the solvent is compatible with the body site in which the final solution will be placed. If that is not the case, the homogeneous mixture must first be dried, then placed in a solvent that is compatible with the body site in which the final solution will be placed. One of ordinary skill in the art will be able to select the specific solution based on the chemical properties of the active agent and the viscoelastic compound, as well as the concentration of active agent that is desired to have in the solution.

In one embodiment, stirring according to the invention involves tumbling of the product. Such tumbling may be accomplished by any means known in the art. Alternatively, the stirring may be accomplished using standard, relatively low-shear mixing techniques. This may be contrasted with classical pharmaceutical compounding, where solutions are stirred in a much more vigorous manner (e.g., propeller mixing or a V-blender).

When using standard mixing equipment such as a static mixer, the mixing will take more than about six hours. For a process when sodium hyaluronate of an average molecular mass of 5-6 millions is mixed with aqueous solution to render a 1% (w/w) sodium hyaluronate solution, the mixing time is preferable more than 8 hours. More preferably about 12 hours, all in room temperature. It is conceived by the present inventors, that mixing the dry polymer compound with a solution of active agents, besides improved homogeneity significantly reduces the mixing time and the risk of any remaining entrapped air in the final preparation. Unlike the instance where the active compound is mixed with a viscoelastic that is in solution, the mixing with the dry viscoelastic compound generally does not shear the viscoelastic compound to any great amount. When the dry viscoelastic compound is mixed with the active agent to a homogeneous mixture in accordance with the present invention, the molecular weight of the viscoelastic compound is generally not affected to any great extent. This is due to the comparatively short processing time requirements for the viscoelastic solution according to the present invention. In order to achieve a homogeneous solution using known techniques (whereby a solution of active agent is mixed with a viscoelastic solution or gel) over the same time span, much more vigorous mixing techniques (and hence higher shear forces) is required. Such shear forces significantly effect the viscoelastic properties of the solution, making it less viscous. This reduced production time without loss of viscoelastic properties is highly beneficial when selecting an active agent, as it allows the use of agents that are more sensitive to degradation.

The present invention also provides higher assurance of homogeneity when compared to solutions that are processed according to known techniques, whereby the solution is mixed and the active agent is allowed to dissipate throughout the viscoelastic solution or gel over a period of time. The mixing embodiment of the present invention involves the dissolution of a dry viscoelastic composition or gel into a homogeneous solution of active agent. Since the system is structured to add a dry composition to a homogeneous solution (as opposed to trying to mix two homogeneous solution), such a system reaches homogeneity more reliably and faster.

Spray Coating

A solution according to the present invention may be prepared by spray coating the viscoelastic compound in dry form with the active agent. In such an instance the active agent, in solution, is sprayed towards the dry viscoelastic compound such that the particles of the dry viscoelastic compound become coated with the active agent. The solvent for the active agent must be compatible with the agent (i.e., not attack or prevent the intended working of the active agent) and must not adversely effect the dry viscoelastic agent. Preferably, the solvent is water or a compound which vaporizes more easily than water. One of ordinary skill in the art will be able to select the specific solution based on the chemical properties of the active agent and the viscoelastic compound, as well as the concentration of active agent that is desired to have in the solution. By way of example, and not of limitation, water and/or water-ethanol mixtures are suitable. If required, surplus solvent may be evaporated from the spray coated viscoelastic agent prior to the addition of the water required to make the aqueous homogeneous solution. In one embodiment of the invention, the water-solubility of the active ingredient that is sprayed onto the viscoelastic compound is higher than the water-solubility of the viscoelastic compound.

Unlike the instance where the active compound is mixed with a viscoelastic that is in solution, when the dry viscoelastic compound is spray coated with the active agent to form a homogeneous mixture in accordance with the present invention, and the resulting homogeneous mixture is then placed into solution using low-shear techniques, the molecular weight of the viscoelastic compound is generally not affected to any great extent.

Fluidized Bed Treatment

A solution according to the present invention may be prepared by subjecting the viscoelastic agent to a fluidized bed treatment with the active agent. Systems capable of performing such treatment are known in the art. By way of example, such systems typically have a main chamber fluid bed with an inlet and an outlet. The main chamber may also be equipped with direct or indirect heating. The viscoelastic would be added to the main chamber in particulate form. The active agent may be added to the main chamber in particulate form, or as a solution (e.g., in the case of fluid bed spray granulation). One of ordinary skill in the art will be able to factor in variables such as the chemical properties of the chosen viscoelastic, the chemical properties of the selected active agent, the desired properties of the resulting solution, the capabilities of the fluid bed processing system selected to be used, and the properties of the solvent to design a system to produce a solution according to the present invention.

Unlike the instance where the active compound is mixed with a viscoelastic that is in solution, when the dry viscoelastic compound and active agent are formed into a homogeneous mixture in accordance with the present invention, and the resulting homogeneous mixture is then placed into solution using low-shear techniques, the molecular weight of the viscoelastic compound is generally not affected to any great extent.

Again, the benefit of the present invention (whereby a homogeneous solution is formed on a shorter time scale) is believed to be due to the comparatively short processing time requirements for the viscoelastic solution according to the present invention. In order to achieve a homogeneous solution using known techniques over the same time span, much more vigorous mixing techniques (and hence higher shear forces) would be required. Such shear forces would change the viscoelastic properties of the solution. This reduced production time is highly beneficial when selecting an active agent, as it allows the use of agents that are more sensitive to degradation. A second benefit of the present invention is that it provides a higher assurance of homogeneity. When a homogeneous mixture of the dry viscoelastic compound and active agent is placed into solution, it very quickly forms a homogeneous solution.

Rewet Agglomeration

A solution according to the present invention may be prepared by subjecting the viscoelastic agent to a particle aggregation process known as rewetting agglomeration. Systems capable of performing such treatment are known in the art. By way of example, such systems typically have an agglomeration chamber where a powder (the viscoelastic agent) is dispersed in the air and contacted with a spray of liquid (active agent, in solvent). Moist, porous agglomerates are formed. As one of ordinary skill in the art will appreciate, such agglomerates may be dried. One of ordinary skill in the art will be able to factor in variables such as the chemical properties of the chosen viscoelastic, the chemical properties of the selected active agent, the desired properties of the resulting solution, the capabilities of the agglomerating system selected to be used, and the properties of the solvent to design a system to produce a solution according to the present invention.

The benefit of the present invention (whereby a homogeneous solution is formed on a shorter time scale) is believed to be due to the comparatively short processing time requirements for forming a homogeneous viscoelastic solution according to the present invention. In order to achieve a homogeneous solution using known techniques over the same time span, much more vigorous mixing techniques (and hence higher shear forces) would be required. Such shear forces would change the viscoelastic properties of the solution. This reduced production time is highly beneficial when selecting an active agent, as it allows the use of agents that are more sensitive to degradation. A second benefit of the present invention is that it provides a higher assurance of homogeneity. When a homogeneous mixture of the dry viscoelastic compound and active agent is placed into solution, it very quickly forms a homogeneous solution. The speed of the dissolution may be controlled by the selection and/or molecular weight of the polymer component. When a comparatively low molecular weight viscoelastic agent is used, the dissolution may be accomplished in a relatively short period of time. With a relatively low molecular weight viscoelastic compound, the dissolution to form a homogeneous solution may be accomplished in under 15 minutes, and preferably under 10 minutes, or as little as less than 5 minutes. With a relatively high molecular weight viscoelastic compound, the dissolution time to form a homogeneous solution may take upwards of an hour or several hours.

FIG. 1 is a view of a syringe which may be used to deliver a solution according to the present invention. In this embodiment, the homogeneous viscoelastic/active agent mixture is placed in a first chamber 11 of a multi-chamber syringe 10. A second chamber 12, which is separated from the first chamber 10 by a stopper 14, contains a solvent. The syringe 10 is defined by a barrel 16, having an inner 18 and an outer 20 portion. The inner side 18 of the syringe 10 defines at least one channel 22. When the end 24 of the syringe 10 is depressed, the stopper 14 moves down the barrel 16 so that the channel 22 allows fluid communication between the first chamber 11 and the second chamber 12. In one embodiment of the invention, the homogeneous mixture is placed into the syringe under vacuum so no air bubbles are present in the final homogeneous solution. The syringe according to this embodiment of the present invention allows for the preparation of a homogeneous solution immediately prior to use. This may be particularly important when degradation of active agent is an issue.

One of ordinary skill in the art will realize that other configurations of the above-described syringe are suitable for use in association with the present invention, and it is sufficient that the syringe be capable of initially maintaining the homogeneous mixture and solvent apart, yet also being configured to allow them to mix upon demand. Alternatively, other forms of packaging that are initially maintaining the homogeneous mixture and solvent apart, yet also being configured to allow them to mix upon demand are suitable. For example, the homogeneous viscoelastic/active agent mixture may be held in a bottle that is in fluid communication with a second bottle, separated by a stopper. The user exerts a force, which moves the stopper into the second bottle, thereby allowing the contents of the two bottles to mix. If the product was desired to be used in a syringe, the user could then draw up an appropriate quantity of homogeneous viscoelastic/active agent solution/gel. An example of such a product configuration is utilized by Novartis AG with the univial that is used to package their acetylcholine chloride intraocular solution (trade name MIO-CHOL®-E).

There are numerous ways in which solutions according to the present invention may be used. By placing the active agent in a homogeneous viscoelastic solution, it is possible to carefully control dosage (particularly when compared to a solution that is not homogeneous). As will be appreciate by one of skill in the art, dosage is important from two viewpoints: to ensure that the patient receives sufficient quantity of active agent to achieve adequate results, and to ensure that the patient does not receive too much active agent which, depending on the active agent, could be toxic to the patient. This feature is important in eye surgery as described herein, but could also be useful with regard to injections. The viscoelastic solution or gel will dissipate within a body at a slower rate than most solvents which are currently used to deliver active agents. This will allow the doctor to control the amount and concentration of active agent that is delivered to a patient, as well as the timing of the administration of the active agent. The dosage and rate of dissipation may be controlled by the viscosity of the solution and concentration of active agent.

In one embodiment the method of treating posterior chamber opacification includes at least two ways of attacking the epithelial cells, for example by employing two different agents with capacity to kill or inhibit the cells with different mechanisms, such as a cytotoxic agent in combination with an agent that can rupture cell membranes or compromise their integrity.

In one aspect the aqueous viscoelastic solution is hypotonic which means that it comprises water with a salinity of less than 0.9%, aiming at destroying epithelial cells through osmotic pressure. Preferably the salinity is below 0.6% and more preferably below 0.3%.

In another aspect the aqueous viscoelastic solution is hypertonic and comprises salts with a concentration above 0.9%.

In another aspect the aqueous viscoelastic solution is isotonic.

The aqueous solution can include one or more agents that can kill or inhibit epithelial cells from proliferation. Such agents can be cytotoxic agent, surfactants, divalent cation chelators, antibodies or analogs directed against epithelial cellattachment receptors, agents or vectors that comprises a nucleic acid including a gene that induces cell death (apoptosis), basement membrane binding agents conjugated to cytotoxic compounds.

By way of example, and not of limitation, cytotoxic agents can be selected among saporin, ricin, methotrexate, 5-fluorouracil, daunomycin, doxorubicin, mitoxanthrone, vinca alkaloids, vinblastine, colchicine, cytochasins, monensin, mitomycin and ouabain. Most preferably the cytotoxic agent is methotrexate, 5-fluorouracil, saporin, mitomycin, doxorubicin and/or Actinomycin-D.

Agents or vectors that comprise nucleic acid comprise one or mire genes coding for a protein inducing cell death by necrosis and the genes coding for proteins toxic for the lens epithelial cells, preferably said agent is a chosen from a gene coding for an agent inducing apoptosis, or a gene involved in the process of apoptosis, most preferably said agent is chosen from among the genes coding for p53, BAX, FLICE (also called caspase 8) TRAIL and TRAIL-R. Furthermore, said one or more agents include a molecule of nucleic acid comprising a gene coding for an agent inducing the death of the lens epithelial cells, under a transcriptional control specific to said cells. One particularly useful agent comprises a vector of the adenovirus type carrying an apoptosis gene is described in WO 02/094177 (Malecaze).

In a more specific embodiment, the present invention refers to a method of preventing capsular opacification following cataract surgery comprising the steps of filling the anterior chamber of the eye with a first viscoelastic agent followed by surgically removing the defect lens from the capsular bag and introducing a second viscoelastic solution or gel with one or more active agents homogenously distributed therein into the capsular bag. The so introduced second viscoelastic contacts the inner wall of the capsular bag with said second viscoelastic agent for a time sufficient to effective kill remaining epithelial cells, whereupon it is removed. The second viscoelastic agent is prepared according to what has been mentioned above, may be hypotonic as above and includes one or more agents for killing or inhibit proliferation of epithelial cells according to the foregoing discussion. The first viscoelastic agent is preferably an agent with adhesive and dispersive properties that is capable of providing an efficient protection of the ocular tissues during the surgical intervention and admits an efficient sealing capacity of the capsular bag during the introduction of the second viscoelastic solution or gel engaged in epithelial cell killing step. Healon® GV OVD or Healon® 5 OVD are suitable first viscoelastic agents. The lens removal process can follow conventional and establish procedures involving phacoemulsification and will not be described in detail.

The methods and tools to treat capsular opacification described above can be incorporated in conventional lens replacement methods including surgical implantation of intraocular lenses. In a preferred embodiment, they are a part of a lens surgical lens replacement that includes filling of the capsular bag with lens forming fluid that is able to cure in-situ in the eye to form a lens implant that can undergo accommodation. Such systems are disclosed in more detail for example WO 01/76651 and will not described here in more detail. Following the treatment steps directed at prevention from capsular opacification, this form of lens replacement ocular surgery includes the steps of providing the empty capsular bag with a sealing plug capable of admitting fluid communication for a capsule filling material, filling the capsular bag with lens forming material, sealing the capsule with the plug and removing the first viscoelastic material. Suitable plugs for the lens filling process are found in WO 02/043630 which document describes sealing devices that can be manipulated for fluid entrance into the capsular bag, subsequently positioned for resealing in their permanent location.

Viscoelastic compositions or gels as prepared in accordance with the present invention can have further utilities for administration active agents to a body site when a product homogeneity is required. Non-limiting examples refer to topically administrable compositions or gels prepared according to the present invention of aqueous compositions hyaluronic acid and therapeutic agent for administration to the eye surface and to compositions of hyaluronic acid and therapeutic agent adapted to be suitable as artificial tears, for example as outlined in U.S. Pat. No. 5,770,628.

EXEMPLIFYING PART OF THE INVENTION

Example 1

Preparations of 1.0% sodium hyaluronate solutions with and without cycloheximide.

The aim was to prepare two 1.0% w/w sodium hyaluronate solutions. The first one is sodium hyaluronate in sterilized demineralised water, and the second is sodium hyaluronate together with cycloheximide in sterilized demineralised water. Both solutions were transferred to sterilized cartridges and packed in pre-sterilized pouches. The pouches were stored in the refrigerator at ±4° C. The sodium hyaluronate solutions will be used in tests to prevent cell growth in the eye.

First cycloheximide had to be added to one tube with sterilized demineralised water. Added was ~250 mg cycloheximide to the tube, which was shaken for about a minute to mix the contents. The set-up for stirring the sodium hyaluronate solutions was built in a Laminar Air Flow (LAF) bench.

The sodium hyaluronate (molecular mass $M_{rm}$ of 4,000,000 Da) was weighed in cleaned beakers of 100 ml (50 mg each). Sterilized demineralised water (49.5 ml) was added to the first beaker and cycloheximide in sterilized demineralised water (49.5 ml) was added to the other one. Both gave 1.0% w/w sodium hyaluronate solutions.

Both solutions were stirred, by electric motor with stirrer, for at least 12 hours. After the sodium hyaluronate was completely dissolved, as judged visually, the solutions were both transferred to sterilized cartridges. The cartridges were packed in pre-sterilized pouches and: stored in the refrigerator until needed.

Filled were a total of 4½ cartridges with 1.0% w/w sodium hyaluronate solution in demineralised water and 4½ cartridges with 1.0% w/w sodium hyaluronate solution in cycloheximide-demineralised water.

Example 2

Aqueous Solution of Actinomycin-D and Cycloheximide.

A solution of 10 µg/ml Actinomycin-D and 25 µg/ml Cycloheximide is prepared with sterile double distilled water (named Solution AC). The natural left lens of 4 New-Zealand white rabbits (named Series A) is removed through a 1 mm diameter capsular rhexis, while the AC (anterior chamber) is filled with a viscoelastic (Healon® OVD), the empty capsule is rinsed during 5 minutes with Solution AC with a double loop cannula. After 5 minutes the solution is removed by rinsing with balanced salt solution (BSS). One such suitable BSS is available from Advanced Medical Optics, Inc., Santa Ana, Calif. under the trade name Endosol.

After implanting a plug in the empty capsule, the capsule is filled with a lens capsule filling lens forming material. A plug is brought into position to close the capsule. The viscoelastic is removed out of the AC and the eye is closed with a suture.

The same surgery is performed on another series of 4 New-Zealand white rabbits (named Series B), but the step of rinsing the capsule with Solution AC is left out. This is the control series.

The left eyes of the rabbits are inspected after 2, 4, 8 and 12 weeks. The results after 12 weeks are shown in Table 1. In conclusion, Series B developed very rapidly a secondary cataract, caused by lens epithelial cell proliferation. The corneas stayed clear. The left capsules of series A stayed practically clear, but in a number of eyes the corneas showed hazy areas.

Viscoelastic Solution of Actomycin-D and Cycloheximide.

A solution of 10 µg/ml Actinomycin-D and 25 µg/ml Cycloheximide is made in sterile double distilled water. 1 wt % dry sodium hyaluronate is dissolved in this solution by thorough mixing during 12 h at room temperature in accordance with Example 1. The final solution (named Solution HAC) is highly viscous and shows the viscoelastic behaviour of a 1% hyaluronate solution. The natural left lens of 4 New-Zealand white rabbits (named Series C) is removed through a 1 mm diameter capsular rhexis, while the AC is filled with a viscoelastic (Healon GV® viscoelastic solution—available from Advanced Medical Optics, Inc., Santa Ana, Calif.). The empty capsule is filled with Solution HAC. After 5 minutes the solution is removed by aspiration and the capsule is rinsed with balanced salt solution (BSS). After implanting a plug in the empty capsule, the capsule is filled with a capsular filling lens forming material. The plug is brought into position to close the capsule. The viscoelastic is removed out of the AC and the eye is closed with a suture.

The left eyes of the rabbits are inspected after 2, 4, 8 and 12 weeks. The results after 12 weeks are also shown in Table 1. In conclusion, Series C developed no secondary cataract and the corneas stayed clear.

The results can be compared with the control series B and with series A.

TABLE 1

Corneal opacities and Secondary Cataract formation 12 weeks after treatment:

| Series | Treatment   | Corneal opacity | Sec. Cataract |
|--------|-------------|-----------------|---------------|
| A      | Solution AC | yes             | no            |
| B      | Control     | no              | yes           |
| C      | Solution HAC| no              | no            |

Example 3

A solution of 10 µg/ml Actomycin-D and 25 µg/ml cycloheximide is made in sterile double distilled water. 2 wt % dry HPMC ($M_{rm}$ 80.000) is dissolved in this solution by thorough mixing during 12 h at room temperature in accordance with Example 1. The final solution shows the viscoelastic behaviour of a normal 2% HPMC-80.000 MWt solution. When tested, the solution shows the same results as the hyaluronate/actomycin-D/cycloheximide solution described above.

Example 4

A rhesus monkey I (weight around 5 kg) was anesthetised and placed under the operating microscope (Zeiss, Oberkochen, Germany) with the left eye facing to the microscope. This eye was iridectomized 4 to 6 weeks before. An eyelid speculum was placed and a 3 mm corneal incision was made with a keratome. The anterior chamber was filled with Healon GV® OVD. Then a 30G needle on a 2 cc syringe was used to puncture the anterior capsule. The capsule was lifted with the needle to start a small flap. This flap was then grasped with Utrata forceps and a capsulorhexis of 1-1.5 mm was created. A paracentesis was created with a 30 degree knife and an anterior chamber maintainer connected to an infusion bottle containing BSS with 5000 IU of heparin was inserted in the eye. The lens substance was removed through a 30G needle by aspiration.

After removal of the lens substance, the anterior chamber maintainer was blocked and the anterior chamber was filled with Healon® OVD.

The empty capsule is filled with Solution HAC. After 5 minutes the solution is removed by aspiration and the capsule is rinsed with BSS. After implanting a plug in the empty capsule, the capsule is filled with a capsular filling lens forming material. The plug is brought into position to close the capsule. The viscoelastic is removed out of the AC and the eye is closed with a suture.

The same surgery is performed on another rhesus monkey II, but the step of rinsing the capsule with Solution HAC is left out. This is the control series.

The left eyes of both monkeys were inspected on a regular base until 30 weeks after surgery.

Two weeks after surgery slit-lamp inspection of the left eye of monkey II already revealed the beginning of capsular opacification. This became more severe after each inspection. Also the refraction of the eye (measured with a Zeiss-Hartinger refractometer) became increasingly more myopic, suggesting a rounding up of the lens capsule, probably because of capsular shrinkage. 2 weeks after surgery the refraction was −1D. After 30 weeks the refraction was between −10 and −12D.

The center of the refilled lens of monkey I remained clear during the whole testing period and the refraction of the eye did not change (and was measured around −1.5D), suggesting the absence of capsular shrinkage as a result of the capsular treatment with the HAC solution.

Example 5

Visco-elastic Solution of Actomycin-D and D, L-Methotrexate.

A solution of 10-5 mol/l (10 μg/ml) Actomycin-D and 10-5 mol/l (4.5 μg/ml) D, L-Methotrexate is made in sterile double distilled water. 1 wt % dry hyaluronic acid (MW 4,000,000 DA) is dissolved in this solution by thorough mixing during 12 h at room temperature in accordance with Example 1. The final solution (named Solution HAM) is highly viscous and shows the viscoelastic behaviour of a 1% hyaluronate solution. The natural left lens of 2 New-Zealand white rabbits (named Series D) is removed through a 1 mm diameter capsular rhexis, while the AC is filled with a viscoelastic (Healon GV® OVD, available from Advanced Medical Optics, Inc., Santa Ana, Calif.). The empty capsule is filled with Solution HAM. After 5 minutes the solution is removed by aspiration and the capsule is rinsed with BSS. After implanting a plug in the empty capsule, the capsule is filled with a capsular filling lens forming material. The plug is brought into position to close the capsule. The viscoelastic is removed out of the AC and the eye is closed with a suture.

The left eyes of the rabbits were inspected in regular intervals of 1, 3, 6, 9 and 12 months post-operatively. The eyes and the corneas stayed clear. Capsules and lenses did not show secondary cataract.

Two 5 year old rhesus monkeys were give the same treatment as described in Example 4, but the empty capsule was filled with Solution HAM instead of solution HAC. Directly post-op the corneas stayed clear and at the 1 month inspection no secondary cataract was noted.

What is claimed is:

1. A method of performing ocular surgery while preventing capsular opacification comprising the steps of:
   (i) filling the anterior chamber of the eye with a first aqueous viscoelastic agent;
   (ii) surgically removing the defective lens from the capsular bag;
   iii) introducing a second viscoelastic agent with one or more active agents that effectively prevents capsular opacification whereby the second viscoelastic agent in combination with the active agent is dissimilar to the first aqueous viscoelastic agent, wherein the second viscoelastic agent in combination with the active agent is homogenously distributed in the capsular bag, wherein said active agent is selected from the group consisting of a cytotoxic agent, an anti-proliferative agent, a cell growth inhibiting agent, and mixtures thereof and further wherein the homogenous distribution of the second viscoelastic agent and the one or more active agents is accomplished by mixing a dry viscoelastic compound and the at least one active agent with a method selected from the group consisting of (a) mixing a viscoelastic compound in dry form with a solution of the active agent, (b) mixing using particle aggregation techniques, and then placing the homogeneous mixture in solution, (c) spray coating the viscoelastic compound in dry form with the active agent, and then placing the coated viscoelastic compound in solution, (d) fluidized bed pelletizing, and then placing the pellets into solution, (e) container blending the dry viscoelastic compound with the active agent to form a homogeneous mixture, and then placing the mixture in solution, (f) forming a homogeneous mixture using fluid bed granulation, and then placing the mixture in solution, (g) using fluid bed coating to form a homogeneous mixture of dry viscoelastic compound and active agent, and then placing the mixture in solution (h) spheronizing the dry viscoelastic compound and active agent to form a homogeneous mixture, and then placing the mixture in solution, (i) using dram coating to form a homogeneous mixture of dry viscoelastic compound and active agent, and then placing the mixture in solution, (j) using sieve technology to form a homogeneous mixture of dry viscoelastic compound and active agent, and then placing the mixture in solution, (k) using wet granulation to form a homogeneous mixture of dry viscoelastic compound and active agent, and then placing the mixture in solution, (n) using semi-continuous granulation to form a homogeneous mixture of dry viscoelastic compound and active agent, and then placing the mixture in solution, and (m) using fluid bed drying to form a homogeneous mixture of dry viscoelastic compound and active agent, and then placing the mixture in solution;
   (iv) contacting the inner wall of the capsular bag with said second viscoelastic agent for a time sufficient to effectively kill or inactivate remaining epithelial cells; and
   (v) removing the second viscoelastic agent.

2. A method according to claim 1 further comprising a rinsing step following the removal of the second viscoelastic agent.

3. A method according to claim 2, wherein the rinsing step employs irrigation with a balanced salt solution.

4. A method of performing lens replacement ocular surgery including the method of claim 1 and further:
   (a) providing the empty capsular bag with a sealing plug capable of admitting fluid communication for a capsule filling material;
   (b) filling the capsular bag with lens forming material;
   (c) sealing the capsule with the plug and
   (d) removing the first viscoelastic material.

5. A method according claim 4, wherein the lens forming material is allowed to form an accommodating lens implant.

* * * * *